(12) United States Patent
Titz (10) Patent No.: US 9,371,351 B2
(45) Date of Patent: Jun. 21, 2016

(54) **GLYCOMIMETICS AS *PSEUDOMONAS AERUGINOSA* LECTIN INHIBITORS**

(71) Applicant: Universität Konstanz, Constance (DE)

(72) Inventor: Alexander Titz, Kreuzlingen (DE)

(73) Assignee: Universität Konstanz, Constance (DE)

( * ) Notice: Subject to any disclaimer, the term of this patent is extended or adjusted under 35 U.S.C. 154(b) by 6 days.

(21) Appl. No.: 14/391,109

(22) PCT Filed: Apr. 9, 2013

(86) PCT No.: PCT/EP2013/001047
§ 371 (c)(1),
(2) Date: Oct. 7, 2014

(87) PCT Pub. No.: WO2013/152848
PCT Pub. Date: Oct. 17, 2013

(65) Prior Publication Data
US 2015/0361122 A1    Dec. 17, 2015

(30) Foreign Application Priority Data

Apr. 10, 2012 (EP) .................................... 12002531

(51) Int. Cl.
| | | |
|---|---|---|
| *C07H 7/02* | (2006.01) | |
| *C07H 7/04* | (2006.01) | |
| *C07H 7/06* | (2006.01) | |
| *C07H 15/04* | (2006.01) | |
| *C07D 309/02* | (2006.01) | |
| *C07D 309/10* | (2006.01) | |
| *C07D 407/12* | (2006.01) | |
| *A61K 31/351* | (2006.01) | |
| *A61K 31/7028* | (2006.01) | |
| *A61K 45/06* | (2006.01) | |

(52) U.S. Cl.
CPC .............. *C07H 15/04* (2013.01); *A61K 31/351* (2013.01); *A61K 31/7028* (2013.01); *A61K 45/06* (2013.01); *C07D 309/02* (2013.01); *C07D 309/10* (2013.01); *C07D 407/12* (2013.01); *C07H 7/02* (2013.01); *C07H 7/04* (2013.01); *C07H 7/06* (2013.01)

(58) Field of Classification Search
None
See application file for complete search history.

(56) References Cited

FOREIGN PATENT DOCUMENTS

| WO | 2007021721 A2 | 2/2007 |
|---|---|---|
| WO | 2007143052 A1 | 12/2007 |

OTHER PUBLICATIONS

Carchon et al., Tetrahedron Letters, 42, 2001, pp. 8821-8824.*
Huang et al., Molecules, 2009, 14(7), pp. 2447-2457.*
Carchon, et al., "Synthesis of a Non-Charged Analogue of Guanosyldiphosphofucose", Tetrahedron Letters, vol. 42, Oct. 10, 2001, pp. 8821-8824.
Huang, et al., "Synthesis of 3-N-Sugar-Substituted-2, 4(1H, 3H)-Quinazolinediones as Anti-Angiogenesis Agents", Molecules, Jul. 8, 2009, vol. 14, pp. 2447-2457.
PCT Notification of Transmittal of the International Search Report and Written Opinion, International Searching Authority, pp. 1-11.

* cited by examiner

*Primary Examiner* — Traviss C McIntosh, III
(74) *Attorney, Agent, or Firm* — McDonnell Boehnen Hulbert & Berghoff LLP (57) ABSTRACT

The present invention relates to fucose- and mannose-derived glycomimetics and their general use in prophylaxis or treatment of *Pseudomonas aeruginosa* infections including respiratory tract infections, urinary tract infections, nosocomial infections and chronic wound infections in a patient encompassing a patient suffering already from cystic fibrosis. Said glycomimetics are inhibitors of *Pseudomonas aeruginosa* lectin LecB.

15 Claims, 2 Drawing Sheets

GLYCOMIMETICS AS *PSEUDOMONAS AERUGINOSA* LECTIN INHIBITORS

CROSS-REFERENCE

This application is a section 371 of International application no. PCT/EP2013/001047, filed Apr. 9, 2013 which claims priority from EP patent application No. 12002531.7, filed Apr. 10, 2012.

FIELD

The present invention relates to glycomimetics and their general use in prophylaxis or treatment of *Pseudomonas aeruginosa* infections including respiratory tract infections, urinary tract infections, nosocomial infections and chronic wound infections in a patient encompassing a patient suffering already from cystic fibrosis. Said glycomimetics are inhibitors of *Pseudomonas aeruginosa* lectin LecB.

BACKGROUND

*Pseudomonas aeruginosa* is an opportunistic, ubiquitous gram-negative bacterium accounting for a large number of nosocomial infections in immunocompromised hosts. Additionally, it colonizes the lungs of patients suffering from cystic fibrosis, which can ultimately lead to lung failure. Based on the bacterium's high resistance towards antibiotics and the ability to form biofilms, these infections result in a high mortality of the patients. *P. aeruginosa* can switch to the biofilm mode of life, which serves as a physical barrier to survive antibiotic treatment and host immune defense. It is thereby able to maintain chronic infections. In a biofilm, bacteria are embedded in the extracellular matrix. This matrix is very complex and consists mainly of extracellular DNA, polysaccharides (pel, psi and alginate) and proteins. *P. aeruginosa* produces two soluble lectins under quorum-sensing control: LecA (or PA-IL) and LecB (or PA-IIL). These tetrameric carbohydrate binding proteins recognize specific monosaccharide residues in a calcium-dependent manner (C-type lectins). Whereas LecA is specific for D-galactose, LecB can bind L-fucosides and D-mannosides. These saccharide moieties are frequently found on the cell surface of the host and the bacterium and they are subunits of the polysaccharides of the extracellular matrix in the biofilm. Both lectins, LecA and LecB, were shown to be necessary for *P. aeruginosa* biofilm formation, suggesting a structural role for maintenance of the biofilm architecture. Since both lectins are virulence factors and necessary for biofilm formation, their inhibition is considered a promising approach for antipseudomonadal treatment. It has been shown that the inhibition of these lectins with multivalent carbohydrate-based ligands resulted in reduced biofilm formation of *P. aeruginosa* in vitro. Furthermore, inhalation of an aqueous galactose and fucose containing aerosol resulted in a reduction of respiratory tract infections with *P. aeruginosa*.

The treatment of infections with *P. aeruginosa* has been a long-standing problem since antibiotics cannot reach all the bacteria which are embedded within the biofilm. Therefore, there is a need for therapeutic agents that can inhibit the formation of biofilm or disintegrate the biofilm.

LecB has an unusually high affinity for fucose residues. This has been explained by the crystal structure of the complex: two calcium ions in the binding site mediate the binding of one saccharide ligand to the protein.

Lewis$^a$ trisaccharide (α-Fuc1-4(βGal1-3)-GlcNAc) is the best known monovalent ligand of LecB with a K$_d$ value of 210 nM and the crystal structure of the complex revealed an additional hydrogen bond of the GlcNAc-6-OH with the receptor. The remaining part of GlcNAc and the galactose moiety are, however, not in contact with the protein surface. Consequently, known synthetic inhibitors were simplified and based on the Fuc-α-1,4-GlcNAc disaccharide or on fucose alone. The anomeric centers of GlcNAc in Fuc-GlcNAc and of fucose were substituted with functional groups allowing facile conjugation to dendrimers, but also with small substituents to mimic the GlcNAc-6-OH in order to establish the known hydrogen bond with the receptor. This did, however, not lead to an increase in affinity of the resulting molecules when compared to the parent saccharide Lewis$^a$: the disaccharide derivatives had lower dissociation constants than Lewis$^a$ and one monosaccharide derivative an equal dissociation constant to Lewis$^a$. In another example, fucosylamides have been designed for binding to the fucose binding site and for establishing an additional hydrogen bond with LecB, but the affinity was threefold lower than methyl fucoside (Me-α-Fuc: K$_d$=430 nM).

The success of monovalent fucose-based ligands was limited. First, in all known LecB ligands, fucose glycoconjugates are α-linked and, consequently, all synthetic conjugates designed as inhibitors of LecB are terminal α-fucosides without modification of the terminal fucose. This may lead to unwanted, nonspecific binding of these molecules to various fucose-binding receptors in the host, e.g., the selectins, DC-SIGN and the mannose binding lectin. Second, the modifications introduced at the anomeric center failed to increase the binding affinity compared to the parent molecules methyl fucoside or Lewis$^a$. Methyl and p-nitrophenyl β-fucosides have also been investigated and showed strongly reduced affinity for LecB as compared to their alpha-anomers.

LecB also binds mannosides via the 2, 3 and 4 hydroxyl groups that have the same relative orientation of the hydroxyl groups in fucose. Interestingly, the additional 6-OH of mannose is involved in a hydrogen bond to the side chain of Ser23 of LecB.

However, mannose lacks the lipophilic methyl group of fucose which establishes a contact with LecB in the crystal structure. This served as an explanation for the increased affinity of fucose over mannose (Me-α-Man: K$_d$=71 μM) towards LecB.

To date, a non-terminal glycoside, e.g. a modified mannose derivative, has not been known as an inhibitor of the glycoconjugate recognition of LecB. Such a non-terminal glycoside might lead to selective and highly potent *P. aeruginosa* lectin inhibitors, that do not block related lectins of the host's immune system. Moreover, small molecules are more desirable than dendrimers or polymers as orally-administered therapeutic agents.

SUMMARY

Thus, the problem underlying the present invention is to provide novel LecB inhibitors which are useful in prophylaxis and treatment of infections, such as nosocomial infections, of *Pseudomonas aeruginosa* in a patient and respiratory tract infections of a patient suffering from cystic fibrosis, can be preferably administered orally and are selective *P. aeruginosa* lectin inhibitors that should reduce unwanted nonspecific binding of the known *P. aeruginosa* lectin inhibitors.

The solution to the above technical problem is achieved by the embodiments characterized in the claims. In particular, the compounds of the present invention are highly selective and potent *P. aeruginosa* lectin inhibitors.

The term "methyl α-mannoside" herein means methyl α-D-mannopyranoside and may be also designated hereinafter as methyl mannoside, Me-α-Man or Me-α-D-Man.

In particular, the present invention relates to a compound represented by the following general formula (I), (XVII), (XVIII), or a salt thereof:

(I)

(XVII)

(XVIII)

wherein X is SO$_2$ (sulfonyl) or CO (carbonyl);
R$^1$ is (II)

or (III)

n is 1, 2 or 3;
R$^2$ is a hydrogen atom or an alkyl group having 1 to 3 carbon atoms;
R$^3$ is
(i) an aralkenyl group or an aralkyl group, the alkenyl moiety having 2 to 6 carbon atoms, the alkyl moiety having 1 to 6 carbon atoms and the aryl moiety being preferably a phenyl group or a naphthyl group, wherein the aryl moiety may have one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group, and wherein two adjacent substituents of the aryl moiety may be connected to form a methylenedioxy group or an ethylenedioxy group;
(ii) an aryl group or a heteroaryl group, both of which may have one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group, wherein two adjacent substituents of the aryl group may be connected to form a methylenedioxy group or an ethylenedioxy group, and wherein preferably, if R$^1$ is formula (III), R$^2$ is a hydrogen atom and X is CO, R$^3$ is not an o-nitrophenyl group; or
(iii) a heteroaralkenyl group or a heteroaralkyl group, the alkenyl moiety having 2 to 6 carbon atoms, the alkyl moiety having 1 to 6 carbon atoms and the heteroaryl moiety may have one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group; and R$^4$ is a C$_1$-C$_4$ alkyl group or an aryl group.

According to the present invention, the term "C$_1$-C$_4$ alkyl group" means a straight or branched alkyl group having 1 to 4 carbon atoms, wherein a methyl group or an ethyl group is preferred.

The term "C$_1$-C$_4$ alkoxy group" means a straight or branched alkoxy group having 1 to 4 carbon atoms, wherein a methoxy group or an ethoxy group is preferred.

The term "aralkenyl group" means a group consisting of a straight or branched, substituted or unsubstituted alkenyl moiety having 2 to 6 carbon atoms, and an aryl moiety.

The term "aralkyl group" means a group consisting of a straight or branched, substituted or unsubstituted alkyl moiety having 1 to 6 carbon atoms, and an aryl moiety.

The term "heteroaralkenyl group" means a group consisting of a straight or branched, substituted or unsubstituted alkenyl moiety having 2 to 6 carbon atoms, and a heteroaryl moiety.

The term "heteroaralkyl group" means a group consisting of a straight or branched, substituted or unsubstituted alkyl moiety having 1 to 6 carbon atoms, and a heteroaryl moiety.

The terms "aryl group" and "aryl moiety" include mono-, di- and tricyclic ring systems such as a phenyl group or a naphthyl group, which may be substituted as defined above. Examples of the substituted aryl groups or aryl moieties include 2,4,6-trimethylphenyl, 2,4,6-triisopropylphenyl, p-bromophenyl, p-methylphenyl, o-methoxyphenyl, 3,4-dimethoxyphenyl, 3,4-methylenedioxyphenyl, p-nitrophenyl, o-chlorophenyl and p-chlorophenyl groups. In one embodiment, the aryl group or aryl moiety is an unsubstituted phenyl group.

The terms "heteroaryl group" and "heteroaryl moiety" include mono-, di- and tricyclic ring systems such as pyridyl, pyrimidinyl, thienyl and oxazoyl groups, which may be substituted as defined above.

The halogen atom refers to a fluorine, chlorine, bromine or iodine atom.

In a preferred embodiment of the compound of the present invention, n is 1 in formula (II) or (III).

Further, when n is 2, the moiety of the formula (II) or (III) is preferably substituted with a hydroxyl group, wherein the moiety of the formula (I) has preferably one of the following structures:

In another embodiment of the compound of the present invention, $R^2$ in formula (I) is preferably a hydrogen atom or a methyl group, wherein a hydrogen atom is more preferred.

In another embodiment of the compound of the present invention, $R^4$ in formula (I) is preferably a methyl group, an ethyl group or a phenyl group, wherein a methyl group is the most preferred.

In another embodiment of the compound of the present invention, the aryl moiety, the heteroaryl moiety, the aryl group or the heteroaryl group of $R^3$ may have one or more substituents selected from the group consisting of a halogen atom, $-NH_2$, $-NO_2$ and a methoxy group, or two adjacent substituents of the aryl moiety or the aryl group may be connected to form a methylenedioxy group or an ethylenedioxy group, more preferably a methylenedioxy group. The halogen atom is preferably a chlorine atom or a bromine atom.

In another embodiment of the compound of the present invention, X is $SO_2$. In a more preferred embodiment of the compound of the present invention, X is $SO_2$ and $R^3$ is represented by the formula (IV):

(IV)

wherein $R^6$ to $R^{10}$ are independently selected from the group consisting of a hydrogen atom, a halogen atom, $-NH_2$, $-NO_2$, $-CN$, $-OH$, a $C_1$-$C_4$ alkyl group, a $C_1$-$C_4$ alkoxy group and $-COOR^5$ wherein $R^5$ is a hydrogen atom or a $C_1$-$C_4$ alkyl group; or wherein either $R^6$ and $R^7$, or $R^7$ and $R^8$, or $R^8$ and $R^9$, or $R^9$ and $R^{10}$, are connected to form a methylenedioxy group or ethylenedioxy group.

In another embodiment of the compound of the present invention, X is C=O. In a more preferred embodiment of the compound of the present invention, X is CO and $R^3$ is represented by the formula (V):

(V)

wherein $R^6$ to $R^{10}$ are independently selected from the group consisting of a hydrogen atom, a halogen atom, $-NH_2$, $-NO_2$, $-CN$, $-OH$, a $C_1$-$C_4$ alkyl group, a $C_1$-$C_4$ alkoxy group and $-COOR^5$ wherein $R^5$ is a hydrogen atom or a $C_1$-$C_4$ alkyl group; or wherein either $R^6$ and $R^7$, or $R^7$ and $R^8$, or $R^8$ and $R^9$, or $R^9$ and $R^{10}$, are connected to form a methylenedioxy group or an ethylenedioxy group.

In another embodiment of the compound of the present invention, $R^1$ is represented by the formula (II) and n is 1.

In another embodiment of the compound of the present invention, $R^1$ is represented by the formula (III) and n is 1.

In a preferred embodiment of the compound of the present invention, the compound according to the present invention is represented by the following formulae (VI), (VII), (VIII), (IX), (X), (XI), (XII), (XIII), (XIV), (XV), (XVI), (XVII) or (XVIII):

(VI)

(VII)

(VIII)

(IX)

(X)

(XI)

(XII)

(XIII)

(XIV)

(XV)

(VXI)

(XVII)

(XVIII)

A further aspect of the present invention relates to a pharmaceutical composition comprising the compound according to the present invention in a pharmaceutically effective amount. The pharmaceutical composition may further comprise an auxiliary agent, e.g. selected from the group consisting of a pharmaceutically acceptable carrier, diluent, salt, buffer and excipient. The pharmaceutical composition may additionally comprise one or more anti-bacterial therapeutic agents.

Further, the pharmaceutical composition may be formulated in any desired form such as tablets, solutions, sprays (aerosols) and ointments, and, depending on the formulation form, the pharmaceutical composition may be administered via inhalation, oral administration, topical administration, intravenous route, intramuscular route, peritoneal route or subcontaneous route.

The compound or the pharmaceutical composition according to the present invention can be used in prophylaxis or treatment of *Pseudomonas aeruginosa* infections in a patient, for example nosocomial *Pseudomonas aeruginosa* infections. Further, the compound or the pharmaceutical composition according to the present invention can be used in prophylaxis or treatment of *Pseudomonas aeruginosa*-associated respiratory tract infections, urinary tract infections, nosocomial infections and chronic wound infections in a patient, particularly in a patient suffering already from cystic fibrosis, for example a chronic infection of the respiratory tract.

The present compound may be used in combination with one or more anti-bacterial therapeutic agent(s) for the therapeutic applications as described above.

According to the present invention, the term "patient" encompass any mammal, preferably a human being. The patient may be an immunocompromised patient, for example suffering from pneumonia, urinary tract infection, meningitis, mucoviscidosis or acquired immunodeficiency syndrome (AIDS).

The present invention will be further illustrated in the following examples without any limitation thereto.

The compound according to the present invention exhibits an excellent LecB binding activity, and thus possess an anti-LecB inhibitory activity.

The dosage of the compound or the pharmaceutical composition according to the present invention may depend on symptoms and age of a patient, the type of administration, etc. The suitable dosage may be determined by a person skilled in the art.

The present invention also relates to a method of treatment, wherein the compound or the pharmaceutical composition of the present invention is administered to a patient for preventing or treating infections of *Pseudomonas aeruginosa*.

EXAMPLES

Example 1

Fluorescence Polarization Assay for LecB

A LecB competition assay was carried out by a novel fluorescence polarization assay developed by the inventors of the present invention. To date, an enzyme-linked lectin assay (ELLA) is widely used for the evaluation in screening of the binding potential of ligands to LecB. This allows the evaluation of molecules over a broad affinity range, including monovalent ligands and oligomeric dendrimers thereof. ELLAs have been developed based on enzyme-linked immunosorbent assays (ELISA). Since lectins display much lower affinities to their saccharide ligands than antibodies to the corresponding antigens used in ELISAs, the ELLAs suffer from poor reproducibility between different plates. This poor reproducibility likely results from the numerous handling steps involved in this assay format, i.e., coating of the reference ligand or the lectin, blocking, incubation, detection and numerous washing steps in between. Furthermore, the current ELLA protocol involves either a surface immobilization of LecB or a covalent modification of the lectin, which could interfere with ligand binding. Consequently, hits from the ELLA are usually further characterized by direct measurement of the binding process of the ligand with the native, unmodified protein using microcalorimetry, requiring large amounts of protein.

The developed fluorescence polarization method/assay for LecB is a good way to circumvent the disadvantages of the ELLA protocol. In this assay format, the displacement of a fluorescently-labeled reporter ligand bound to the receptor by an inhibitor can be measured by mixing protein, inhibitor and reporter ligand in a given buffer system. This not only allows the reduction of numerous handling steps of an ELLA, but also allows the direct analysis of the binding process of the molecule of interest with the native, unmodified LecB in solution. Furthermore, the assay format has been downscaled from 96-well plates to a 384-well plate format requiring low amounts of protein, reporter ligands and test compounds.

Two reporter ligands with fluorescein linked through an ethyl spacer to α-fucoside (3) or α-mannoside (5), respectively, were synthesized according to Scheme 1 below. The fucose-based reporter ligand 3 was obtained from a lanthanum triflate-catalyzed fucosylation of 2-bromoethanol following the procedure of Dasgupta et al. (Dasgupta S, Rajput V K, Roy B, Mukhopadhyay B. J Carb Chem. 2007, 26(2), 91-106.) in an anomeric ratio of α/β=4:1. Acetylation of 2-bromoethyl fucoside, nucleophilic replacement of the bromide by sodium azide and deacetylation under Zemplen conditions yielded 2 in good yield. 2-Aminoethyl fucoside (2) was subsequently treated with fluorescein-5-isothiocyanate (FITC) and base to yield the reporter ligand 3 in 96% yield. 2-Azidoethyl α-mannoside (4) was synthesized as pure anomer by glycosylation of 2-bromoethanol with pentaacetyl mannose according to Dahmen et al. (Dahmen J, Frejd T, Gronberg G, Lave T, Magnusson G, Noori G. Carb Res. 1983, 116 (2), 303-307.), followed by nucleophilic displacement of the bromide with $NaN_3$ and Zemplen deacetylation according to Geng et al. (Geng J, Mantovani G, Tao L, Nicolas J, Chen G, Wallis R, Mitchell D A, Johnson B R G, Evans S D, Haddleton D M. J Am Chem Soc. 2007, 129(49), 15156-63.). The mannose-based reporter ligand 5 was obtained after reduction of the azide in 4 and treatment of the resulting amine with FITC.

Scheme 1: Synthesis of fucose-(3) and mannose-(5) based fluorescein-labeled reporter ligands. Reagents and conditions: (i) La(OTf)$_3$, 2-bromoethanol, 7.5 h, 70° C.; (ii) Ac$_2$O, pyridine, 12 h, r.t., 46% (2 steps, α/β 4:1); (iii) NaN$_3$, DMF, 3.25 h, 70° C., 70%; (iv) NaOMe, MeOH, 12 h, r.t.; (v) H$_2$, Pd/C, EtOH, 20 h, r.t., 66% (2 steps); (vi) FITC, NaHCO$_3$, DMF, 6.5 h, r.t., 96%; (vii) H$_2$, Pd/C, EtOH, 22 h, r.t., 98%; (viii) FITC, DMF, 16.5 h, r.t., 79%;

Both fluorescent ligands were subsequently titrated with LecB (FIG. 1) and the binding to the lectin was observed as a change in fluorescence polarization. Fucose-derived 3 (EC$_{50}$=697 nM) is a better ligand to LecB than the mannoside 5 (EC$_{50}$>16 μM), consistent with the known affinities of methyl α-fucoside and methyl α-mannoside for LecB.

Figure 1:
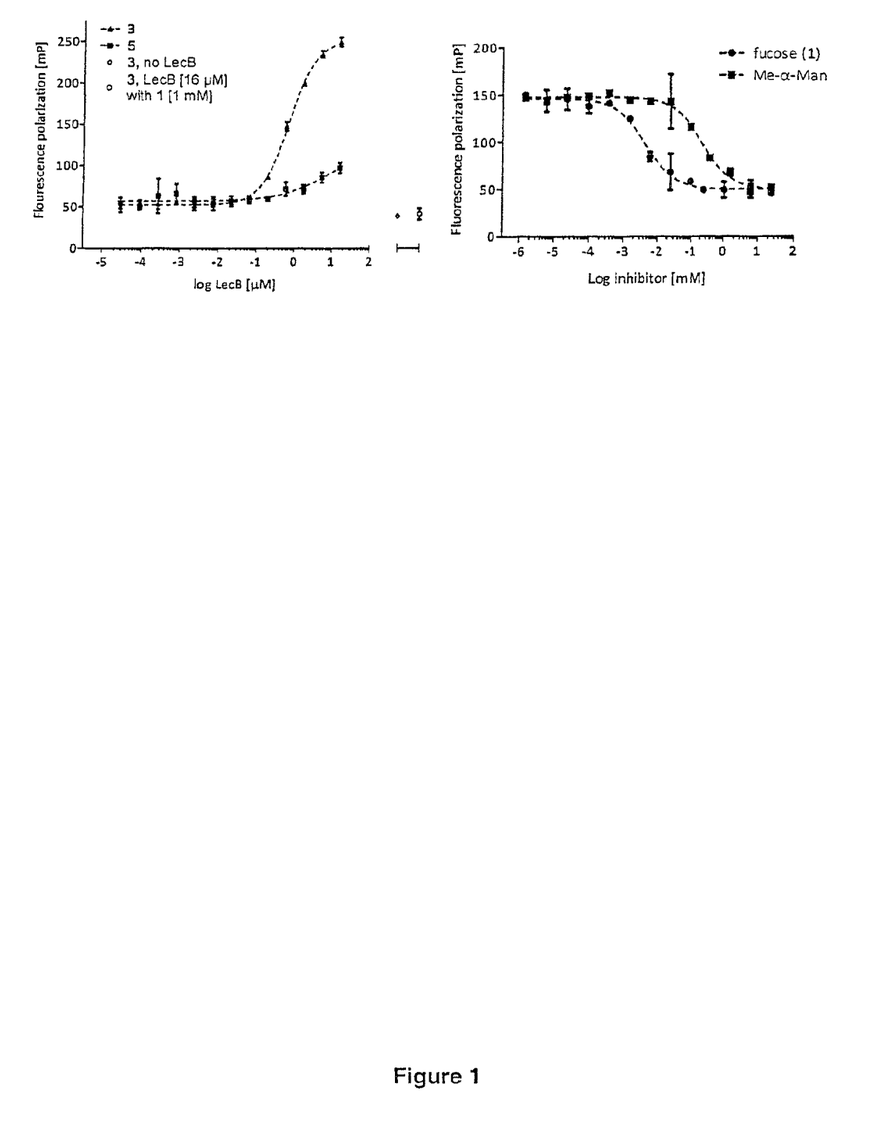
FIG. 1. (left) Titration of fluorescein-labeled reporter ligands 3 (fucose-based) and 5 (mannose-based) with LecB and determination of the fluorescence polarization reveals a strong and specific binding of 3 ($EC_{50}$=697 nM) that could be completely inhibited by the addition of excess fucose (1). Mannose-based 5 showed only a weak binding to LecB ($EC_{50}$>16 μM). (right Competitive inhibition of the binding of 3 to LecB with increasing amounts of inhibitors allowed the determination of $IC_{50}$ values for fucose (1. $IC_{50}$ 3.29±0.86 μM, N=7) and methyl a-mannoside ($IC_{50}$=219±67 μM, N=7).

The controls indicated that binding of 3 to LecB was specific and could be competitively inhibited by addition of excess fucose. Consequently, 3 was chosen as the reporter ligand for the inhibition assays. Similar conditions were applied, but the protein concentration was fixed at 150 nM. Titration of the system with fucose (1) or methyl mannoside indicated a concentration-dependent displacement of the reporter ligand from the protein. The resulting sigmoidal data points on the logarithmic inhibitor concentration scale were used to fit a one-site inhibition model and obtain IC$_{50}$ values.

Typically, to 20 μL of a stock solution of LecB (225 nM) and reporter ligand (1.5 nM) 3 in TBS/Ca$^{2+}$(100 μM) were added 10 μL serial dilutions (10 mM to 128 μM) of testing compounds in TBS/Ca$^{2+}$(100 μM) using a Biotek Precision 2000 robot in triplicates. After addition of the reagents, the microtiter plates were centrifuged at 800 rpm for 1 min at 23° C. and incubated for 6 h at room temperature. The fluorescence was measured on a Tecan INFINITE F500 plate reader (Tecan Austria GmbH) with excitation filters at 485 nm and emission filters at 535 nm in black 384-well microtiter plates (Greiner Bio-One). The G-factor was set on 0.92154 and the gain to 80. The measured intensities were reduced by buffer values. The data were analyzed with Graphpad Prism 5 and fitted according to the four parameter variable slope model. Bottom and top plateaus were defined by the standard compounds fucose and methyl mannoside respectively and the data was reanalyzed with these values fixed.

Synthesis of the Fluorescent Reporter Ligands

2-Bromoethyl 2,3,4-tri-O-acetyl-α-L-fucopyranoside. The title compound was obtained in analogy to Dasgupta et al. (Dasgupta S, Rajput V K, Roy B, Mukhopadhyay B. *J Carb Chem.* 2007, 26(2), 91-106.) To a mixture of L-fucose (1.0 g, 6.1 mmol)) and 2-bromoethanol (4.7 mL, 10.9 eq) in a two-necked flask lanthanum(III)triflate (380 mg, 0.1 eq) was added under argon. The mixture was stirred at 70° C. for 7.5 h. Then, the reaction was quenched with triethylamine (1 mL), concentrated in vacuo and the residue was purified by chromatography (SiO$_2$; CH$_2$Cl$_2$/MeOH gradient 1-5%). The unprotected 2-bromoethyl L-fucopyranoside was obtained as a 4:1 mixture of α/β-anomers as judged by NMR: $^1$H NMR (400 MHz, MeOH-d4) δ 4.85 (d, J=2.9 Hz, 1H, H-1 of α), 4.34-4.26 (m, H-1 of β), 4.14 (q, J=6.3 Hz, 1H, H-5), 3.97 (ddd, J=11.5, 6.8, 6.0 Hz, 1H, OCHaCH$_2$Br), 3.88 (dt, J=11.3, 5.6 Hz, 1H, OCHbCH$_2$Br), 3.80-3.78 (m, 2H, H-2, H-3), 3.71 (br s, 1H, H-4), 3.65-3.62 (m, 2H, CH$_2$Br), 1.31 (d, J=6.5 Hz, CH$_3$ of β), 1.25 (d, J=6.6 Hz, CH$_3$ of α).

The material was subsequently dissolved in pyridine (45 ml) and Ac$_2$O (33 mL) was added dropwise at 0° C. The reaction was allowed to warm to room temperature and was stirred over night. Removal of the volatiles in vacuo and purification by chromatography (SiO$_2$; PE/EtOAc gradient of 15-25%). The title compound 3 was obtained as a white powder (1.12 g, 46.1% over 2 steps, ratio α/β: 4/1).

2-Azidoethyl α-L-fucopyranoside. Bromoethyl fucoside (1.12 g, 2.81 mmol, 4:1 α/β) was dissolved in DMF (17 mL) and NaN$_3$ (1.12 g, 5.0 eq) was added under stirring. Then, the mixture was heated to 70° C. for 3.5 h. After cooling to room temperature, PhMe was added and the mixture was filtered through celite to remove excess NaN$_3$. The filtrate was washed with H$_2$O (2×20 mL), dried over Na$_2$SO$_4$ and filtered. This filtrate was concentrated in vacuo and the residue purified by chromatography (PE/EtOAc gradient 0-100%) to give the acetylated azide (709 mg) in 70.3% yield. The material was dissolved in dry MeOH (22 mL) under argon and freshly prepared NaOMe in MeOH (1 mL) was added. The solution was stirred at room temperature for 18 h after which it was neutralized with Amberlite (IR-120, H$^+$-form), filtered through celite and concentrated in vacuo to give crude azide (525 mg, 4:1 α/β).

TLC (SiO$_2$; CH$_2$Cl$_2$/MeOH 8:1) Rf=0.4

$^1$H NMR (400 MHz, CDCl$_3$) δ 4.90 (d, J=2.5 Hz, 1H, H-1 of α), 4.26 (d, J=7.2 Hz, 1H, H-1 of β), 3.99 (q, J=6.8 Hz, 1H, H-5), 3.93-3.78 (m, 3H), 3.77-3.68 (m, 2H), 3.55-3.38 (m, 2H, CH$_2$N$_3$), 1.32 (d, J=6.5 Hz, CH$_3$ of β), 1.29 (d, J=6.6 Hz, 3H, CH, of α).

$^{13}$C NMR (101 MHz, CDCl$_3$) δ for the a anomer: 98.99 (C-1), 71.93 (C-4), 71.02 (C-3), 68.97 (C-2), 67.03 (OCH2), 66.45 (C-5), 50.78 (CH$_2$N$_3$), 16.25 (CH$_3$).

The NMR data match previously reported one by Patel et al. (Patel A, Lindhorst T. *E J Org Chem* 2002, (1), 79-86.)

2-Aminoethyl α-L-fucopyranoside (2). Crude azide (525 mg, 4:1 α/β) was dissolved in EtOH (35 mL) and Pd/C (10%, 50 mg) was added. The mixture was vigorously stirred for 20 h under H$_2$ (1 atm) at room temperature. The suspension was filtered through celite and filtrate was concentrated in vacuo and purified by chromatography (SiO$_2$; A: CH$_2$Cl$_2$, B: 75% EtOH/25% aqueous NH$_2$OH (25% w/v); gradient of 33% to 85% B). The title compound 2 (303 mg, 66.3%, 4:1 α/β) was obtained as white amorphous solid.

$^1$H NMR (400 MHz, MeOH-d4) δ 4.78 (d, J=2.6 Hz, 1H, H-1 of α), 4.22 (d, J=7.4 Hz, 1H, H-1 of R), 3.96 (q, J=6.6 Hz, 1H, H-5), 3.83-3.73 (m, 3H, OCHa-CH$_2$NH$_2$, H-2, H-3), 3.70 (s, 1H, H-4), 3.53-3.46 (m, 1H, OCHb-CH$_2$NH$_2$), 2.99-2.85 (m, 2H, CH$_2$—NH$_2$), 1.27 (d, J=6.5 Hz, CH, of β), 1.21 (d, J=6.6 Hz, 3H, CH, of α).

$^{13}$C NMR (101 MHz, MeOH-d4) δ 100.69 (C-1), 73.64 (C-4), 71.68 (C-2 or 3), 70.11 (C-3 or 2), 69.43 (OCH$_2$CH$_2$NH$_2$), 67.70 (C-5), 41.89 (CH$_2$NH$_2$), 16.66 (CH$_3$).

The NMR data match previously reported one by Ni et al. (Ni J, Singh S, Wang L. *Bioconjug Chem.* 2003, 14(1), 232-8.)

HRMS: [C$_8$H$_{17}$NO$_5$+H]$^+$ calcd: 208.1180 found: 208.1178; [α]$_D^{23}$=−132 (c=0.1; MeOH)

N-(fluorescein-5-yl)-N'-(α-L-fucopyranosyl ethylen)-thiocarbamide (3). Aminoethyl fucoside 2 (82 mg, 0.35 mmol, 4:1 α/β) was dissolved in dry DMF (5 mL), FITC (154 mg, 1.1 eq) was added and the mixture was stirred for 6.5 h at room temperature. After addition of NaHCO$_3$ (31 mg, 1.0 eq), the mixture was concentrated in vacuo and the residue purified by chromatography (SiO$_2$; CH$_2$Cl$_2$(1% HOAc)/EtOH (2% HOAc) gradient of 5-25%) and the title compound 3 was obtained as orange-red powder (202 mg, 96.3%, 4:1 α/β).

Analysis by reversed phase HPLC (250 mm×4 mm Nucleodur 100-5 C-18; H$_2$O/MeCN 20-90% (v/v), with 0.1% HCO$_2$H, run for 30 min at 0.9 mL/min) resulted in the elution of one narrow peak at 12.0 min retention time.

$^1$H NMR (400 MHz, DMSO-d6) δ 8.21 (d, J=1.4 Hz, 1H, PhH), 7.77 (d, J=7.3 Hz, 1H, PhH), 7.19 (d, J=8.3 Hz, 1H, PhH), 6.68 (d, J=2.0 Hz, 2H, Xanthen-H), 6.65–6.54 (m, 4H, Xanthen-H), 4.67 (d, J=3.3 Hz, 1H, H-1α), 4.48-4.32 (m, 3H, CH$_2$CH$_2$), 3.84 (q, J=6.7 Hz, 1H), 3.79-3.46 (m, 4H, H-2, -3, -4, 1H of CH$_2$CH$_2$), 1.09 (d, J=6.5 Hz, 3H, H-6).

$^{13}$C NMR (151 MHz, DMSO-d6) δ 180.63 (C=S), 168.48 (C=O), 159.43 (2C, Xanthen-C), 151.83 (2C, Xanthen-C), 147.27 (ArC), 141.22 (ArC), 129.51 (ArC), 129.02 (2C, Xanthen-CH), 124.08 (ArCH), 116.41 (ArCH), 112.56 (2C, Xanthen-CH), 109.67 (2C, Xanthen-CH), 103.42 (ArCH), 102.20 (2C, Xanthen-CH), 99.24 (C-1), 82.97 (Xanthen-C), 71.60, 69.68, 68.06 (C-2, -3, -4), 66.91 (C-5), 66.08 (CH$_2$), 43.72 (CH$_2$), 16.57 (C-6).

HRMS: [C$_{29}$H$_{27}$N$_2$O$_{10}$S]$^-$ calcd: 595.1392 found: 595.1381; [α]$_D^{23}$=−23 (c=0.1; MeOH)

N-(fluorescein-5-yl)-N'-(α-D-mannopyranosyl ethylen)-thiocarbamide (5). 2-Aminoethyl a-D-mannopyranoside (Kleinert M, Rockendorf N, Lindhorst T. *Eur J Org Chem* 2004, (18), 3931-3940) (53 mg, 0.28 mmol) was dissolved in DMF (3 mL) and FITC (93 mg, 1.0 eq) was added. The reaction mixture was stirred at room temperature for 17 h, concentrated in vacuo and purified by chromatography (SiO$_2$; CH$_2$Cl$_2$ (1% HOAc)/EtOH (2% HOAc) gradient of 0-57%) to give the title compound as orange solid (115 mg, 78.8%).

$^1$H NMR (400 MHz, MeOH-d4) δ 8.17 (d, J=1.6 Hz, 1H, ArH), 7.79 (dd, J=8.3, 1.9 Hz, 1H, ArH), 7.16 (d, J=8.3 Hz, 1H, ArH), 6.68 (dd, J=5.5, 3.1 Hz, 4H, ArH), 6.55 (dd, J=8.7, 2.3 Hz, 2H, ArH), 4.84 (br s, 1H, H-1), 3.99-3.56 (m, 10H, H-2, -3, -4, -5, -6a,b, 4H of CH$_2$CH$_2$).

$^{13}$C NMR (101 MHz, MeOH-d4) δ 183.13 (C=S), 171.23 (C=O), 161.39 (ArC), 154.19 (ArC), 142.49 (ArC), 130.34 (ArCH), 128.95 (ArCH), 125.67 (ArCH), 113.64 (ArCH), 111.49 (ArCH), 103.55 (ArCH), 101.84 (C-1), 74.86, 72.61, 72.09, 68.64 (C-2, -3, -4, -5), 67.02 (CH$_2$), 62.97 (CH$_2$), 45.36 (CH$_2$).

HRMS: [C$_{29}$H$_{27}$N$_2$O$_{11}$S]$^-$ calcd: 611.1341 found: 611.1320; [α]$_D^{23}$=+40 (c=0.1; MeOH)

Example 2

Synthesis of the Compounds

The compounds according to the present invention were synthesized following the general scheme 2 shown below.

Scheme 2: Synthesis of mannose-derived amides 10 and hybrids 13. Reagents and conditions: (i) TsCl, pyridine, r.t., 24 h; (ii) NaN$_3$, DMF, 70° C., 4 h; (iii) H$_2$, Pd/C, EtOH, r.t., 12 h; (iv) sulfonyl/acyl chlorides or carboxylic acids/EDC*HCl, TEA, DMF; (v) MeNO$_2$, DBU, dioxane, 24 h; (vi) FeSO$_4$, aq. NH$_4$OH, r.t., 10 min;

Methyl 6-amino-6-deoxy-α-D-mannopyranoside (9) was obtained according to the procedure by Wang et al. (WANG, P., SHEN, G., WANG, Y., ICHIKAWA, Y., and WONG, C. *J Org Chem*, 1993, 58(15), 3985-3990.) For the amide (10&11)-derived LecB ligands, the azido group in 7 was reduced with hydrogen and palladium on charcoal. The resulting primary amine 9 was then reacted with either sulfonyl chlorides, acyl chlorides or carbodiimide-activated carboxylic acids to give the corresponding 6-sulfonamido 6-deoxy mannosides 10 or 6-amido 6-deoxy mannosides 11.

For the hybrid structure 13, L-fucose was transformed into a beta-Henry adduct according to Phiasivongsa et al. (Phiasivongsa P, Samoshin V S, Gross P H, Tetrahedron Lett. 2003, 44, 5495-5498). The nitro group was reduced to give 12 in good yield and amides 13 were synthesized as described for 11.

General Procedure for Amide and Sulfonamide Couplings

Crude methyl 6-amino-6-deoxy-α-D-mannopyranoside (50 mg, max. 0.26 mmol), triethylamine (54 µL, 1.5 eq.) and in case of free acids EDC*HCl (73 mg, 1.5 eq) were dissolved in dry DMF (1.5 mL) and cooled to 0° C. Then, the carboxylic acid, the anhydride, the acyl chloride or the sulfonyl chloride (0.31 mmol, 1.2 eq.) dissolved in DMF (0.5 mL) was added dropwise under argon. After stirring for 1 h at 0° C., the reaction was allowed to warm to room temperature and was stirred for further 1-3 days. In case of BzCl, the reaction was complete after 2 h, as judged by TLC. The reactions were quenched with saturated aqueous $NH_4Cl$ (10 mL), and extracted with EtOAc (1×30 mL, 6×10 mL). The combined organic layers were dried over $Na_2SO_4$, filtered and concentrated in vacuo. The residue was purified by chromatography on silica with $CH_2Cl_2$/EtOH or EtOAc/EtOH.

Methyl 6-(phenylsulfonylamido)-6-deoxy-α-D-mannopyranoside (10a) was obtained from phenylsulfonyl chloride in 73% yield (over two steps).

$^1$H NMR (400 MHz, MeOH-d4) δ 7.88 (d, J=7.4 Hz, 2H, ArH), 7.66-7.51 (m, 3H, ArH), 4.55 (d, J=1.0 Hz, 1H, H-1), 3.78-3.73 (m, 1H, H-2), 3.65-3.55 (m, 1H, H-3), 3.51-3.43 (m, 2H, H-4, -5), 3.39-3.29 (m, 1H, H-6a), 3.27 (s, 3H, $OCH_3$), 3.10-2.97 (m, 1H, H-6b).

$^{13}$C NMR (101 MHz, MeOH-d4) δ 142.01 (ArC), 133.64 (ArCH), 130.24 (2C, ArCH), 128.11 (2C, ArCH), 102.60 (C-1), 72.68 (C-4 or -5), 72.32 (C-3), 72.00 (C-2), 69.73 (C-4 or -5), 55.37 ($OCH_3$), 45.49 (C-6).

HRMS: $[C_{13}H_{19}NO_7S+Na]^+$ calcd: 356.07744, found: 356.07657

Methyl 6-(p-tosylamido)-6-deoxy-α-D-mannopyranoside (10b) was obtained from p-toluenesulfonyl chloride in 28% yield (over two steps).

$^1$H NMR (400 MHz, MeOH-d4) δ 7.76 (d, J=8.2 Hz, 2H, ArH), 7.37 (d, J=8.1 Hz, 2H, ArH), 4.55 (d, J=1.4 Hz, 1H, H-1), 3.74 (dd, J=3.2, 1.6 Hz, 1H, H-2), 3.59 (dd, J=9.0, 3.5 Hz, 1H, H-3), 3.49-3.43 (m, 2H, H-4, -5), 3.36-3.19 (m, 4H, H-6a, $OCH_3$), 3.05-2.94 (m, 1H, H-6b), 2.43 (s, 3H, $PhCH_3$).

$^{13}$C NMR (101 MHz, MeOH-d4) δ 144.57 (ArC), 138.95 (ArC), 130.68 (2C, ArCH), 128.14 (2C, ArCH), 102.54 (C-1), 72.61 (C-4 or -5), 72.24 (C-2), 71.96 (C-3), 69.65 (C-4 or -5), 55.27 ($OCH_3$), 45.41 (C-6), 21.43 ($PhCH_3$).

HRMS: $[C_{14}H_{21}NO_7S+Na]^+$ calcd: 370.09309, found: 370.09239

Methyl 6-(4-bromophenylsulfonylamido)-6-deoxy-α-D-mannopyranoside (10c) was obtained from 4-bromophenylsulfonyl chloride in 68% yield (over two steps).

$^1$H NMR (400 MHz, MeOH-d4) δ 7.83-7.69 (m, 4H), 4.54 (d, J=1.6 Hz, 1H, H-1), 3.75 (dd, J=3.3, 1.7 Hz, 1H, H-2), 3.64-3.56 (m, 1H, H-3), 3.51-3.43 (m, 2H, H-4, -5), 3.39-3.32 (m, 1H, H-6a), 3.26 (s, 3H, $OCH_3$), 3.11-3.01 (m, 1H, H-6b).

$^{13}$C NMR (101 MHz, MeOH-d4) δ 141.32 (ArC), 133.36 (2C, ArCH), 129.89 (2C, ArCH), 127.99 (ArC), 102.51 (C-1), 72.57 (C-4 or -5), 72.22 (C-3), 71.89 (C-2), 69.60 (C-4 or -5), 55.28 ($OCH_3$), 45.39 (C-6).

HRMS: $[C_{13}H_{18}BrNO_7S+Na]^+$ calcd: 433.98796, found: 433.98643

Methyl 6-(4-nitrophenylsulfonylamido)-6-deoxy-α-D-mannopyranoside (10d) was obtained from 4-nitrophenylsulfonyl chloride in 25% yield (over two steps).

$^1$H NMR (400 MHz, MeOH-d4) δ 8.42-8.38 (m, 2H, ArH), 8.13-8.09 (m, 2H, ArH), 4.51 (d, J=1.6 Hz, 1H, H-1), 3.74 (dd, J=3.3, 1.7 Hz, 1H, H-2), 3.65-3.54 (m, 1H, H-3), 3.50-3.38 (m, 3H, H-4, -5, -6a), 3.26 (s, 3H, $OCH_3$), 3.15-3.09 (m, 1H, H-6b).

$^{13}$C NMR (101 MHz, MeOH-d4) δ 151.37 (ArC), 148.02 (ArC), 129.52 (2C, ArCH), 125.30 (2C, ArCH), 102.58 (C-1), 72.67 (C-4 or -5), 72.25 (C-3), 71.91 (C-2), 69.52 (C-4 or -5), 55.30 ($OCH_3$), 45.39 (C-6).

HRMS: $[C_{13}H_{18}N_2O_9S+Na]^+$ calcd: 401.06252, found: 401.06080

Methyl 6-(2,4,6-trimethylphenylsulfonylamido)-6-deoxy-α-D-mannopyranoside (10e) was obtained from 2,4,6-trimethylphenylsulfonyl chloride in 84% yield (over two steps).

$^1$H NMR (400 MHz, MeOH-d4) δ 7.02 (s, 2H, ArH), 4.54 (d, J=1.6 Hz, 1H, H-1), 3.74 (dd, J=3.3, 1.7 Hz, 1H, H-2), 3.59-3.55 (m, 1H, H-3), 3.50-3.41 (m, 2H, H-4, -5), 3.27 (s, 3H, $OCH_3$), 3.26-3.20 (m, 1H, H6a), 3.09-3.01 (m, 1H, H-6b), 2.63 (s, 6H, 2×$ArCH_3$), 2.30 (s, 3H, $ArCH_3$).

$^{13}$C NMR (101 MHz, MeOH-d4) δ 143.44 (ArC), 140.34 (2C, ArC), 135.50 (ArC), 132.91 (2C, ArCH), 102.66 (C-1), 72.55 (C-4 or -5), 72.22 (C-3), 71.97 (C-2), 69.74 (C-4 or -5), 55.30 ($OCH_3$), 44.65 (C-6), 23.14 (2C, $ArCH_3$), 20.90 ($ArCH_3$).

Methyl 6-(2,4,6-triisopropylphenylsulfonylamido)-6-deoxy-α-D-mannopyranoside (10f) was obtained from 2,4,6-triisopropylphenylsulfonyl chloride in 43% yield (over two steps).

$^1$H NMR (400 MHz, MeOH-d4) δ 7.28 (s, 2H, ArH), 4.62 (br s, 1H, H-1), 4.26 (septet, J=6.7 Hz, 2H, $CH(CH_3)_2$), 3.80 (br s, 1H, H-2), 3.69-3.51 (m, 3H, H-3, -4, -5), 3.40-3.29 (m, 4H, H-6a, $OCH_3$), 3.14 (dd, J=13.0, 6.8 Hz, 1H, H-6b), 2.96 (septet, J=6.9 Hz, 1H, $CH(CH_3)_2$), 1.37-1.25 (m, 18H, 3×$CH(CH_3)_2$).

$^{13}$C NMR (101 MHz, MeOH-d4) δ 154.02 (ArC), 151.84 (2C, ArC), 134.01 (ArC), 124.88 (2C, ArCH), 102.70 (C-1), 72.59 (C-4 or -5), 72.28 (C-3), 72.00 (C-2), 69.77 (C-4 or -5), 55.38 ($OCH_3$), 44.78 (C-6), 35.38 ($CH(CH_3)_2$), 30.65 (2C, $CH(CH_3)_2$), 25.26 (4C, $CH(CH_3)_2$), 24.00 (2C, $CH(CH_3)_2$).

Methyl 6-(trans-β-styrenesulfonylamido)-6-deoxy-α-D-mannopyranoside (14) was obtained from 9 and trans-β-styrenesulfonyl chloride in 71% yield (over two steps).

$^1$H NMR (400 MHz, MeOH-d4) δ 7.59 (dd, J=6.6, 2.9 Hz, 2H, ArH), 7.46-7.39 (m, 4H, 3 ArH, 1 olefin-H), 7.05 (d, J=15.5 Hz, 1H, olefin-H), 4.61 (d, J=1.6 Hz, 1H, H-1), 3.78 (dd, J=3.4, 1.7 Hz, 1H, H-2), 3.67-3.59 (m, 1H, H-3), 3.59-3.51 (m, 2H, H-4, -5), 3.47 (dd, J=13.5, 2.3 Hz, 1H, H-6a), 3.32 (s, 3H, $OCH_3$), 3.19 (dd, J=13.5, 6.6 Hz, 1H, H-6b). $^{13}$C NMR (400 MHz, MeOH-d4) δ 141.53 (olefin-C), 134.45 (ArC), 131.59 (ArCH), 130.08 (2C, ArCH), 129.30 (2C, ArCH), 127.31 (olefin-C), 102.69 (C-1), 72.80 (C-Man), 72.31 (C-Man), 71.97 (C-Man), 69.66 (C-Man), 55.31 ($OCH_3$), 45.20 (C-6).

HRMS: $[C_{15}H_{21}NO_7SNa]^+$ calcd: 382.09309, found: 382.09312;

N-(6S-Methyl-3R,4R,5R-trihydroxy-tetrahydropyranosyl-2R-methyl)-2,4,6-trimethylphenyl sulfonamide (13b) 2R-aminomethyl-6S-methyl-3R,4R,5R-trihydroxy-tetrahydropyrane (12, 50 mg) and triethylamine (54 μL, 0.39 mmol) were dissolved in dry DMF (1.5 mL) and MeOH (1 mL) and cooled to 0° C. Then, 2,4,6-trimethylphenylsulfonyl chloride (2.5 eq) dissolved in DMF (1 mL) was added dropwise under argon and the reaction was subsequently allowed to warm to room temperature and was stirred for 5 d. The reactions was quenched with saturated aqueous $NH_4Cl$ (20 mL), and extracted with EtOAc (1×60 mL, 5×20 mL). The combined organic layers were dried over $Na_2SO_4$, filtered and concentrated in vacuo. The residue was purified by chromatography on silica ($CH_2Cl_2$/EtOH, gradient of 0-20%) and the title compound was obtained as amorphous solid (79 mg, 72%).

$^1$H NMR (400 MHz, MeOH-d4) δ 7.01 (s, 2H, ArH), 3.56 (d, J=3.1 Hz, 1H), 3.41-3.21 (m, 4H), 3.03-2.91 (m, 2H), 2.62 (s, 6H, 2$ArCH_3$), 2.29 (s, 3H, $ArCH_3$), 1.17 (d, J=6.5 Hz, 3H, $CH_3$). $^{13}$C NMR (101 MHz, MeOH-d4) δ 143.43 (ArC), 140.29 (2C, ArC), 135.62 (ArC), 132.86 (2C, ArCH), 79.17 (CH), 76.29 (CH), 75.51 (CH), 73.52 (CH), 69.80 (CH), 44.91 ($CH_2$), 23.05 (2C, $ArCH_3$), 20.90 ($ArCH_3$), 17.01 ($CH_3$).

HRMS: $[C_{16}H_{25}NO_6S+H]^+$ calcd: 360.14753 found: 360.14757

N-(6S-Methyl-3R,4R,5R-trihydroxy-tetrahydropyranosyl-2R-methyl)-trans-β-styrene sulfonamide (15) was synthesized from 12 and trans-β-styrenesulfonyl chloride in 61% yield. $^1$H NMR (400 MHz, MeOH-d4) δ 7.61-7.56 (m, 2H, ArCH, olefin-CH), 7.45-7.39 (m, 4H, ArCH, olefin-CH), 7.03 (d, J=15.5 Hz, 1H, olefin-CH), 3.64-3.61 (m, 1H), 3.56 (q, J=6.6 Hz, 1H), 3.50-3.40 (m, 3H, 1H of $CH_2$), 3.30-3.23 (m, 1H), 3.16 (dd, J=13.1, 6.9 Hz, 1H, 1H of $CH_2$), 1.21 (d, J=6.5, 1H). $^{13}C$ NMR (101 MHz, MeOH-d4) δ 141.54 (olefin-CH), 134.46 (ArC), 131.57 (ArCH), 130.07 (2C, ArCH), 129.30 (2C, ArCH), 127.25 (olefin-CH), 79.85 (CH), 76.33 (CH), 75.57 (CH), 73.56 (CH), 69.67 (CH), 45.37 ($CH_2$), 17.13 ($CH_3$).

HRMS: $[C_{15}H_{21}NO_6S+H]^+$ calcd: 344.11623 found: 344.11680

Methyl 6-(cinnamido)-6-deoxy-α-D-mannopyranoside (11a) was obtained from cinnamic acid in 56% yield (over two steps).

$^1H$ NMR (400 MHz, MeOH-d4) δ 7.60-7.51 (m, 3H, 2×ArH, olefin-H), 7.41-7.30 (m, 3H, ArH), 6.69 (d, J=15.8 Hz, 1H, olefin-H), 4.65 (d, J=1.5 Hz, 1H, H-1), 3.81 (dd, J=3.3, 1.7 Hz, 1H, H-2), 3.70-3.63 (m, 3H, H-3, -6a,b), 3.62-3.51 (m, 2H, H-4, -5), 3.36 (s, 3H, $OCH_3$).

$^{13}C$ NMR (101 MHz, MeOH-d4) δ 169.11 (C=O), 141.95 (olefin-CH), 136.30 (ArC), 130.83 (ArCH), 129.94 (2×ArCH), 128.83 (2×ArCH), 121.69 (olefin-CH), 102.86 (C-1), 72.46 (C-4, or -5), 72.23 (C-3), 72.06 (C-2), 69.50 (C-4, or -5), 55.23 ($OCH_3$), 41.54 (C-6).

HRMS: $[C_{16}H_{21}NO_6+H]^+$ calcd: 324.14416, found: 324.14361

Methyl 6-(2-methoxycinnamido)-6-deoxy-α-D-mannopyranoside (11b) was obtained from 2-methoxycinnamic acid in 56% yield (over two steps).

$^1H$ NMR (400 MHz, MeOH-d4) δ 7.87 (d, J=15.9 Hz, 1H, olefin-H), 7.55-7.51 (m, 1H, ArH), 7.36-7.30 (m, 1H, ArH), 7.03-6.99 (m, 1H, ArH), 6.97-6.92 (m, 1H, ArH), 6.74 (d, J=15.9 Hz, 1H, olefin-H), 4.64 (d, J=1.6 Hz, 1H, H-1), 3.88 (s, 3H, $PhOCH_3$), 3.81 (dd, J=3.4, 1.7 Hz, 1H, H-2), 3.68 (dd, J=9.0, 3.4 Hz, 1H, H-3), 3.66-3.55 (m, 4H, H-3, -4, -5, -6a,b), 3.35 (s, 3H; Man-$OCH_3$).

$^{13}C$ NMR (101 MHz, MeOH-d4) δ 169.76 (C=O), 159.62 (ArC), 137.33 (olefin-CH), 132.19 (ArCH), 129.37 (ArCH), 124.87 (ArC), 121.93 (olefin-CH), 121.74 (ArCH), 112.40 (ArCH), 102.84 (C-1), 72.47 (C-4 or -5), 72.22 (C-3), 72.05 (C-2), 69.47 (C-4 or -5), 56.02 ($PhOCH_3$), 55.23 (Man-$OCH_3$), 41.51 (C-6).

HRMS: $[C_{17}H_{23}NO_7+H]^+$ calcd: 354.15473, found: 354.15397

Methyl 6-(2-nitrocinnamido)-6-deoxy-α-D-mannopyranoside (11c) was obtained from 2-nitrocinnamic acid in 52% yield (over two steps).

$^1H$ NMR (400 MHz, MeOH-d4) δ 8.03-7.98 (m, 1H, ArH), 7.91 (d, J=15.6 Hz, 1H, olefin-H), 7.80-7.75 (m, 1H, ArH), 7.74-7.68 (m, 1H, ArH), 7.62-7.55 (m, 1H, ArH), 6.67 (d, J=15.6 Hz, 1H, olefin-H), 4.65 (d, J=1.5 Hz, 1H, H-1), 3.81 (dd, J=3.4, 1.7 Hz, 1H, H-2), 3.72-3.57 (m, 5H, H-3, -4, -5, -6a,b), 3.37 (s, 3H, $OCH_3$).

$^{13}C$ NMR (101 MHz, MeOH-d4) δ 167.95 (C=O), 150.15 (ArC), 136.90 (olefin-CH), 134.53 (ArCH), 131.70 (ArC), 131.27 (ArCH), 129.92 (ArCH), 126.65 (olefin-CH), 125.69 (ArCH), 102.85 (C-1), 72.37 (C-4 or -5), 72,24 (C-3), 72.05 (C-2), 69.52 (C-4 or -5), 55.27 ($OCH_3$), 41.61 (C-6).

HRMS: $[C_{16}H_{20}N_2O_8+Na]^+$ calcd: 391.11119, found: 391.11077

Methyl 6-(2-methylcinnamido)-6-deoxy-α-D-mannopyranoside (11e) was obtained from 2-methylcinnamic acid in 52% yield (over two steps).

$^1H$ NMR (400 MHz, MeOH-d4) δ 7.88 (d, J=15.7 Hz, 1H, olefin-H), 7.60-7.54 (m, 1H, ArH), 7.29-7.14 (m, 3H, ArH), 6.60 (d, J=15.7 Hz, 1H, olefin-H), 4.65 (d, J=1.6 Hz, 1H, H-1), 3.81 (dd, J=3.4, 1.7 Hz, 1H, H-2), 3.71-3.51 (m, 5H, H-3, -4, -5, -6a,b), 3.36 (s, 3H, $OCH_3$), 2.41 (s, 3H, $PhCH_3$).

$^{13}C$ NMR (101 MHz, MeOH-d4) δ 169.22 (C=O), 139.57 (olefin-CH), 138.54 (ArC), 135.01 (ArC), 131.73 (ArH), 130.62 (ArH), 127.37 (ArH), 127.07 (ArH), 122.65 (olefin-CH), 102.86 (C-1), 72.46 (C-4 or -5), 72.22 (C-3), 72.05 (C-2), 69.49 (C-4 or -5), 55.23 ($OCH_3$), 41.55 (C-6), 19.75 ($PhCH_3$).

HRMS: $[C_{17}H_{23}NO_6+H]^+$ calcd: 338.15981, found: 338.15902

Methyl 6-(3-nitrocinnamido)-6-deoxy-α-D-mannopyranoside (11f) was obtained from 3-nitrocinnamic acid in 49% yield (over two steps).

$^1H$ NMR (400 MHz, MeOH-d4) δ 8.40 (s, 1H, ArH), 8.23-8.16 (m, 1H, ArH), 7.98-7.89 (m, 1H, ArH), 7.68-7.56 (m, 2H, ArH+olefin-H), 6.85 (d, J=15.8 Hz, 1H, olefin-H), 4.65 (br s, 1H, H1), 3.83-3.78 (m, 1H, H-2), 3.73-3.64 (m, 3H, H-3, -6a,b), 3.63-3.51 (m, 2H, H-4, -5), 3.36 (s, 3H, $OCH_3$).

$^{13}C$ NMR (101 MHz, MeOH-d4) δ 168.15 (C=O), 150.10 (ArC), 139.24 (olefin-CH), 138.20 (ArC), 134.70 (ArCH), 131.26 (ArCH), 124.95 (olefin-CH), 124.86 (ArCH), 122.95 (ArCH), 102.86 (C-1), 72.39 (C-3, -4 or -5), 72.22 (C-3, -4 or -5), 72.04 (C-2), 69.50 (C-3 or -5), 55.26 ($OCH_3$), 41.60 (C-6).

HRMS: $[C_{16}H_{20}N_2O_8+Na]^+$ calcd: 391.11119, found: 391.11070

Methyl 6-(4-methoxycinnamido)-6-deoxy-α-D-mannopyranoside (11h) was obtained from 4-methoxycinnamic acid in 55% yield (over two steps).

$^1H$ NMR (400 MHz, MeOH-d4) δ 7.54-7.46 (m, 3H, 2×ArH, olefin-H), 6.97-6.90 (m, 2H, ArH), 6.55 (d, J=15.8 Hz, 1H, olefin-H), 4.64 (d, J=1.6 Hz, 1H, H1), 3.83-3.79 (m, 4H, $PhOCH_3$, H-2), 3.68 (d, J=8.9, 3.4 Hz, 1H, H-3), 3.66-3.50 (m, 4H, H-4, -5, -6a,b), 3.35 (s, 3H, $ManOCH_3$).

$^{13}C$ NMR (101 MHz, MeOH-d4) δ 169.56 (C=O), 162.60 (ArC), 141.74 (olefin-CH), 130.44 (2C, ArCH), 128.85 (ArC), 119.09 (olefin-CH), 115.34 (2C, ArCH), 102.85 (C-1), 72.50 (C-4 or -5), 72.22 (C-3), 72.05 (C-2), 69.48 (C-4 or -5), 55.82 ($PhOCH_3$), 55.23 ($ManOCH_3$), 41.50 (C-6).

HRMS: $[C_{17}H_{23}NO_7+H]^+$ calcd: 354.15473, found: 354.15432

Methyl 6-(4-nitrocinnamido)-6-deoxy-α-D-mannopyranoside (11i) was obtained from 4-nitrocinnamic acid in 74% yield (over two steps).

$^1H$ NMR (600 MHz, MeOH-d4) δ 8.27-8.21 (m, 2H, ArH), 7.80-7.75 (m, 2H, .ArH), 7.61 (d, J=15.8 Hz, 1H, olefin-H), 6.86 (d, J=15.8 Hz, 1H, olefin-H), 4.65 (d, J=1.5 Hz, 1H, H-1), 3.81 (dd, J=3.3, 1.6 Hz, 1H, H-2), 3.71-3.58 (m, 4H, H-3, -5, -6a,b), 3.54 (t, J=9.4 Hz, 1H, H-4), 3.36 (s, 3H, $OCH_3$).

$^{13}C$ NMR (151 MHz, MeOH-d4) δ 168.03 (C=O), 149.57 (ArC), 142.69 (ArC), 139.19 (olefin-CH), 129.68 (2C, ArCH), 126.11 (olefin-CH), 125.06 (2C, ArCH), 102.87 (C-1), 72.41, 72.22 (C-3 and C-5), 72.04 (C-2), 69.52 (C-4), 55.25 ($OCH_3$), 41.65 (C-6).

HRMS: $[C_{16}H_{20}N_2O_8+H]^+$ calcd: 369.12924, found: 369.12805

Methyl 6-(4-methylcinnamido)-6-deoxy-α-D-mannopyranoside (11k) was obtained from 4-methylcinnamic acid in 52% yield (over two steps).

$^1H$ NMR (400 MHz, MeOH-d4) d 7.52 (d, J=15.7 Hz, 1H, olefin-H), 7.47-7.41 (m, 2H, H-ArH), 7.22-7.18 (m, 2H, ArH), 6.63 (d, J=15.8 Hz, 1H, olefin-H), 4.64 (d, J=1.6 Hz, 1H, H-1), 3.81 (dd, J=3.4, 1.7 Hz, 1H, H-2), 3.68 (d, J=9.0, 3.4 Hz, 1H, H-3), 3.65-3.55 (m, 4H, H-4, -5, -6a,b), 3.35 (s, 3H, $OCH_3$), 2.35 (s, 3H, $PhCH_3$).

$^{13}$C NMR (101 MHz, MeOH-d4) δ 169.34 (C=O), 141.96 (olefin-CH), 141.31 (ArC), 133.53 (ArC), 130.58 (2C, ArCH), 128.84 (2C, ArCH), 120.58 (olefin-CH), 102.85 (C-1), 72.47 (C-4 or -5), 72.22 (C-3), 72.06 (C-2), 69.49 (C-4 or -5), 55.22 (OCH$_3$), 41.52 (C-6), 21.38 (PhCH$_3$).

HRMS: [C$_{17}$H$_{23}$NO$_6$+H]$^+$ calcd: 338.15981, found: 338.15875

Methyl 6-(4-chlorocinnamido)-6-deoxy-α-D-mannopyranoside (11l) was obtained from 4-chlorocinnamic acid in 46% yield (over two steps).

$^1$H NMR (400 MHz, MeOH-d4) δ 7.57-7.48 (m, 3H, 2×ArH, olefin-H), 7.42-7.35 (m, 2H, ArH), 6.69 (d, J=15.8 Hz, 1H, olefin-H), 4.64 (d, J=1.5 Hz, 1H, H-1), 3.80 (dd, J=3.3, 1.6 Hz, 1H, H-2), 3.68 (dd, J=9.0, 3.5 Hz, 1H, H-3), 3.67-3.55 (m, 4H, H-4, -5, -6a,b), 3.35 (s, 3H, OCH$_3$).

$^{13}$C NMR (101 MHz, MeOH-d4) δ 168.79 (C=O), 140.45 (olefin-CH), 136.51 (ArC), 135.07 (ArC), 130.26 (2C, ArCH), 130.11 (2C, ArCH), 122.52 (olefin-CH), 102.87 (C-1), 72.45 (C-4 or -5), 72.21 (C-3), 72.04 (C-2), 69.51 (C-4 or -5), 55.23 (OCH$_3$), 41.57 (C-6).

HRMS: [C$_{16}$H$_{20}$ClNO$_6$+Na]$^+$ calcd: 380.08714, found: 380.08594

Methyl 6-(2,4-dichlorocinnamido)-6-deoxy-α-D-mannopyranoside (11m) was obtained from 2,4-dichlorocinnamic acid in 38% yield (over two steps).

$^1$H NMR (400 MHz, MeOH-d4) δ 7.90 (d, J=15.7 Hz, 1H, olefin-H), 7.74-7.67 (m, 1H, ArH), 7.56-7.51 (m, 1H, ArH), 7.39-7.33 (m, 1H, ArH), 6.72 (d, J=15.7 Hz, 1H, olefin-H), 4.64 (d, J=1.5 Hz, 1H, H-1), 3.80 (dd, J=3.3, 1.6 Hz, 1H, H-2), 3.71-3.55 (m, 5H, H-3, -4, -5, -6a,b), 3.36 (s, 3H, OCH$_3$).

$^{13}$C NMR (101 MHz, MeOH-d4) δ 168.21 (C=O), 136.88 (ArC), 136.27 (ArC), 136.23 (olefin-CH), 133.24 (ArC), 130.78 (ArCH), 129.70 (ArCH), 128.86 (ArCH), 125.28 (olefin-CH), 102.88 (C-1), 72.43 (C-4 or -5), 72.23 (C-3), 72.06 (C-2), 69.52 (C-4 or -5), 55.25 (OCH$_3$), 41.63 (C-6).

HRMS: [C$_{16}$H$_{19}$Cl$_2$NO$_6$+H]$^+$ calcd: 392.06622, found: 392.06469

Methyl 6-(3,4-dimethoxycinnamido)-6-deoxy-α-D-mannopyranoside (11n) was obtained from 3,4-dimethoxycinnamic acid in 33% yield (over two steps).

$^1$H NMR (400 MHz, MeOH-d4) δ 7.49 (d, J=15.7 Hz, 1H, olefin-H), 7.19-7.15 (m, 1H, ArH), 7.14-7.10 (m, 1H, ArH), 6.99-6.93 (m, 1H, ArH), 6.57 (d, J=15.7 Hz, 1H, olefin-H), 4.64 (d, J=1.5 Hz, 1H, H-1), 3.86 (s, 3H, PhOCH$_3$), 3.85 (s, 3H, PhOCH$_3$), 3.80 (dd, J=3.3, 1.6 Hz, 1H, H-2), 3.68 (dd, J=9.0, 3.4 Hz, 1H, H-3), 3.65-3.55 (m, 4H, H-4, -5, -6a,b), 3.36 (s, 3H, ManOCH$_3$).

$^{13}$C NMR (101 MHz, MeOH-d4) δ 169.49 (C=O), 152.29 (ArC), 150.74 (ArC), 141.97 (olefin-CH), 129.37 (ArC), 123.31 (ArCH), 119.44 (olefin-CH), 112.75 (ArCH), 111.34 (ArCH), 102.88 (C-1), 72.49 (C-4 or -5), 72.22 (C-3), 72.07 (C-2), 69.49 (C-4 or -5), 56.46 (ArOCH$_3$), 56.42 (ArOCH$_3$), 55.24 (ManOCH$_3$), 41.51 (C-6).

HRMS: [C$_{18}$H$_{25}$NO$_8$+H]$^+$ calcd: 384.16529, found: 384.16427

Methyl 6-(3,4-methylenedioxycinnamido)-6-deoxy-α-D-mannopyranoside (11o) was obtained from 3,4-methylenedioxycinnamic acid in 59% yield (over two steps). $^1$H NMR (400 MHz, DMSO-d6) δ 7.35 (d, J=15.7 Hz, 1H, olefin-H), 7.15-7.11 (m, 1H, ArH), 7.09-7.03 (m, 1H, ArH), 6.97-6.91 (m, 1H, ArH), 6.59 (d, J=15.7 Hz, 1H, olefin-H), 6.06 (s, 2H, OCH$_2$), 4.51 (d, J=1.4 Hz, 1H, H-1), 3.65 (dd, J=13.7, 1.9 Hz, 1H, H-6a), 3.59 (dd, J=3.3, 1.6 Hz, 1H, H-2), 3.44 (dd, J=8.7, 3.4 Hz, 1H, H-3), 3.39-3.17 (m, 6H, H-4, -5, 6b, OCH$_3$).

$^{13}$C NMR (101 MHz, DMSO-d6) δ 165.53 (C=O), 148.42 (ArC), 147.91 (ArC), 138.58 (olefin-CH), 129.32 (ArC), 123.18 (ArCH), 120.14 (olefin-CH), 108.57 (ArCH), 106.20 (ArCH), 101.41 (OCH$_2$O), 101.10 (C-1), 71.57 (C-4 or -5), 70.33 (C-3), 70.06 (C-2), 68.07 (C-4 or -5), 54.05 (OCH$_3$), 40.15 (C-6).

HRMS: [C$_{17}$H$_{21}$NO$_8$+H]$^+$ calcd: 368.13399, found: 368.13342

Methyl 6-(benzoylamido)-6-deoxy-α-D-mannopyranoside (11p) was obtained from benzoyl chloride in 61% yield (over two steps).

$^1$H NMR (400 MHz, MeOH-d4) δ 7.86-7.81 (m, 2H, ArH), 7.57-7.50 (m, 1H, ArH), 7.49-7.42 (m, 2H, ArH), 4.64 (d, J=1.5 Hz, 1H, H-1), 3.80 (dd, J=3.3, 1.6 Hz, 1H, H-2), 3.77-3.63 (m, 4H, H-3, -5, -6a,b), 3.57 (t, J=9.4 Hz, 1H, H-4), 3.33 (s, 3H, OCH$_3$).

$^{13}$C NMR (101 MHz, MeOH-d4) δ 170.80 (C=O), 135.68 (ArC), 132.67 (ArCH), 129.54 (2C, ArCH), 128.37 (2C, ArCH), 102.83 (C-1), 72.41 & 72.28 (C-3, C-5), 72.03 (C-2), 69.93 (C-4), 55.16 (OCH$_3$), 42.14 (C-6).

HRMS: [C$_{14}$H$_{19}$NO$_6$+Na]$^+$ calcd: 320.11046, found: 320.1099

Methyl 6-(phenylacetamido)-6-deoxy-α-D-mannopyranoside (11q) was obtained from phenylacetic acid in 28% yield (over two steps).

$^1$H NMR (400 MHz, DMSO-d6) δ 8.09 (t, J=5.8 Hz, 1H, NH), 7.31-7.23 (m, 4H, ArH), 7.22-7.16 (m, 1H, ArH), 4.84 (d, J=5.0 Hz, 1H, OH), 4.77 (d, J=4.6 Hz, 1H, OH), 4.65 (d, J=5.9 Hz, 1H, OH), 4.46 (d, J=1.2 Hz, 1H, H-1), 3.69-3.60 (m, 1H, H-6a), 3.59-3.54 (m, 1H, H-2), 3.46 (d, J=13.7 Hz, 1H, PhCH), 3.40 (d, J=13.6 Hz, 1H, PhCH), 3.38-3.32 (m, 1H, H-3), 3.27-3.19 (m, 2H, H-4, -5), 3.11 (s, 3H, OCH$_3$), 3.00-2.91 (m, 1H, H-6b).

$^{13}$C NMR (101 MHz, DMSO-d6) δ 170.27 (C=O), 136.55 (ArC), 129.00 (2×ArCH), 128.16 (2×ArCH), 126.29 (ArCH), 100.98 (C-1), 71.64 (C-4 or C-5), 70.57 (C-3), 70.19 (C-2), 68.44 (C-4 or C-5), 53.88 (OCH$_3$), 42.35 (PhCH$_2$), 40.30 (C-6).

HRMS: [C$_{15}$H$_{21}$NO$_6$+H]$^+$ calcd: 312.14416, found: 312.14331

Methyl 6-(4-nitrobenzoylamido)-6-deoxy-α-D-mannopyranoside (11r) was obtained from 4-nitrobenzoic acid in 18% yield (over two steps).

$^1$H NMR (400 MHz, MeOH-d4) δ 8.33-8.26 (m, 2H, ArH), 8.04-7.99 (m, 2H, ArH), 4.61 (d, J=1.5 Hz, 1H, H-1), 3.77 (dd, J=3.1, 1.6 Hz, 1H, H-2), 3.76-373 (m, 1H, H-6a), 3.71-3.68 (m, 1H, H-6b), 3.68-3.61 (m, 2H, H-3, H-5), 3.53 (t, J=9.4 Hz, 1H, H-4), 3.31 (s, 3H, OCH$_3$).

$^{13}$C NMR (101 MHz, MeOH-d4) δ 168.73 (C=O), 151.05 (ArC), 141.51 (ArC), 129.83 (2C, ArCH), 124.62 (2C, ArCH), 102.87 (C-1), 72.32 & 72.27 (C-3 & C-5), 72.05 (C-2), 69.87 (C-4), 55.22 (OCH$_3$), 42.34 (C-6).

HRMS: [C$_{14}$H$_{18}$N$_2$O$_8$+H]$^+$ calcd: 343.1136 found: 343.1121; [α]$_D^{23}$=+43 (c=0.1; MeOH)

Methyl 6-(2-chlorobenzoylamido)-6-deoxy-α-D-mannopyranoside (11s) was obtained from 2-chlorobenzoyl chloride in 20% yield (over two steps).

$^1$H NMR (400 MHz, MeOH-d4) δ 7.54-7.36 (m, 4H, ArH), 4.66 (d, J=1.6 Hz, 1H, H-1), 3.83 (dd, J=3.2, 1.7 Hz, 1H, H-2), 3.82-3.58 (m, 5H, H-3, -4, -5, -6a,b), 3.41 (s, 3H, OCH$_3$).

$^{13}$C NMR (101 MHz, MeOH-d4) δ 170.41 (C=O), 137.66 (ArC), 132.15 (ArCH), 132.02 (ArC), 131.03 (ArCH), 130.08 (ArCH), 128.08 (ArCH), 102.83 (C-1), 72.39 & 72.32 (C-3 & C-5), 72.09 (C-2), 69.74 (C-4), 55.41 (OCH$_3$), 41.98 (C-6).

HRMS: [C$_{14}$H$_{18}$ClNO$_6$+H]$^+$ calcd: 332.0895 found: 332.0877; [a]$_D^{23}$=+80 (c=0.1; MeOH)

Methyl 6-(2-naphtoylamido)-6-deoxy-α-D-mannopyranoside (11t) was obtained from 2-naphtoic acid in 11% yield (over two steps).

$^1$H NMR (400 MHz, DMSO-d6) δ 8.68 (t, J=5.7 Hz, 1H, NH), 8.47 (s, 1H, ArH), 8.02-7.92 (m, 4H, ArH), 7.64-7.55 (m, 2H, ArH), 4.98 (d, J=5.2 Hz, 1H, OH), 4.82 (d, J=4.5 Hz, 1H, OH), 4.69 (d, J=5.9 Hz, 1H, OH), 4.51 (d, J=1.2 Hz, 1H, H-1), 3.84-3.74 (m, 1H, H-6a), 3.62-3.58 (m, 1H, H-2), 3.56-3.50 (m, 1H, H-5), 3.49-3.44 (m, 1H, H-3 or -4), 3.43-3.35 (m, 2H, H-6b, H-3 or -4), 3.19 (s, 3H, OCH$_3$).

$^{13}$C NMR (101 MHz, DMSO-d6) δ 166.55 (C=O), 134.10 (ArC), 132.15 (ArC), 131.87 (ArC), 128.87 (ArCH), 127.86 (ArCH), 127.62 (ArCH), 127.57 (ArCH), 127.50 (ArCH), 126.72 (ArCH), 124.21 (ArCH); 101.07 (C-1), 71.33 (C-5), 70.64 (C-3 or -4), 70.21 (C-2), 68.71 (C-3 or -4), 53.89 (OCH$_3$), 41.11 (C-6).

HRMS: [C$_{18}$H$_{21}$NO$_6$+H]$^+$ calcd: 348.14416, found: 348.1433

General Procedure Reduction of the Nitro Group

The reduction of the nitro group in 11c,f,i and for the synthesis of 12 was performed with FeSO$_4$ and aqueous NH$_3$ on a 0.1-0.5 mmol scale according to the procedure by Pribulova et al. (Pribulova B, Petrusova M, Patoprsty, V, Petrus, L *Chem. Papers* 2003, 57, p 287-291) Cinnamides 11c,f,i were purified by column chromatography on silica (CH$_2$Cl$_2$/EtOH, gradient of 10-15%), 12 was used without purification in the next step (12→13).

Methyl 6-(2-aminocinnamido)-6-deoxy-α-D-mannopyranoside (11d) was obtained from nitro derivative 11c in 77% yield.

$^1$H NMR (400 MHz, MeOH-d4) δ 7.77 (d, J=15.6 Hz, 1H, olefin-H), 7.36 (dd, J=7.8, 1.3 Hz, 1H, ArH), 7.12-7.05 (m, 1H, ArH), 6.75 (dd, J=8.1, 0.8 Hz, 1H, ArH), 6.66 (t, J=7.5 Hz, 1H, ArH), 6.52 (d, J=15.6 Hz, 1H, olefin-H), 4.64 (d, J=1.6 Hz, 1H, H-1), 3.81 (dd, J=3.4, 1.7 Hz, 1H, H-2), 3.70-3.51 (m, 5H, H-3, -4, -5, -6a,b), 3.36 (s, 3H, OCH$_3$).

$^{13}$C NMR (101 MHz, MeOH-d4) δ 169.83 (C=O), 148.17 (ArC), 137.91 (olefin-CH), 131.76 (ArCH), 128.11 (ArCH), 121.11 (ArC), 120.50 (olefin-CH), 119.06 (ArCH), 117.83 (ArCH), 102.87 (C-1), 72.51 & 72.23 (C-3 or -5), 72.07 (C-2), 69.46 (C-4), 55.25 (OCH$_3$), 41.51 (C-6).

Methyl 6-(3-aminocinnamido)-6-deoxy-α-D-mannopyranoside (11g) was obtained from nitro derivative 11f in 66% yield.

$^1$H NMR (400 MHz, DMSO-d6) δ 8.17 (t, J=5.8 Hz, 1H, NH), 7.26 (d, J=15.7 Hz, 1H, olefin-H), 7.04 (t, J=7.7 Hz, 1H, ArH), 6.73-6.66 (m, 2H, ArH), 6.63-6.54 (m, 2H, olefin-H, ArH), 5.15 (d, J=8.1 Hz, 2H, NH$_2$), 4.89 (d, J=4.9 Hz, 1H, OH), 4.75 (d, J=4.6 Hz, 1H, OH), 4.63 (d, J=5.9 Hz, 1H, OH), 4.50 (d, J=1.4 Hz, 1H, H-1), 3.70-3.62 (m, 1H, H-6a), 3.59 (dd, J=3.3, 1.5 Hz, 1H, H-2), 3.47-3.41 (m, 1H, H-3), 3.38-3.18 (m, 6H, H-4, -5, -6b, OCH$_3$).

$^{13}$C NMR (101 MHz, DMSO-d6) δ 165.57 (C=O), 148.99 (ArC), 139.69 (olefin-CH), 135.36 (ArC), 129.32 (ArCH), 121.04 (olefin-CH), 115.55 (ArCH), 115.29 (ArCH), 112.26 (ArCH), 101.10 (C-1), 71.60, 70.19, 70.08, 68.23 (C-2, -3, -4, -5), 54.01 (OCH$_3$), 40.21 (C-6).

Methyl 6-(4-aminocinnamido)-6-deoxy-α-D-mannopyranoside (11j) was obtained from nitro derivative 11i in 66% yield.

$^1$H NMR (400 MHz, DMSO-d6) δ 7.94 (t, J=5.7 Hz, 1H, NH), 7.24 (dd, J=15.3, 12.1 Hz, 3H, olefin-H, 2×ArH), 6.55 (d, J=8.5 Hz, 2H, ArH), 6.39 (d, J=15.6 Hz, 1H, olefin-H), 5.54 (br s, 2H, NH$_2$), 4.91 (d, J=4.7 Hz, 1H, OH), 4.74 (d, J=4.5 Hz, 1H, OH), 4.61 (d, J=5.9 Hz, 1H, OH), 4.50 (d, J=1.1 Hz, 1H, H-1), 3.65-3.55 (m, 2H, H2, -6a), 3.47-3.40 (m, 1H, H-3), 3.38-3.13 (m, 6H, H-4, -5, -6b, OCH$_3$).

$^{13}$C NMR (101 MHz, DMSO-d6) δ 166.41 (C=O), 150.45 (ArC), 139.68 (olefin-CH), 129.05 (2C, ArCH), 122.21 (ArC), 115.67 (olefin-CH), 113.68 (2C, ArCH), 101.13 (C-1), 71.70 (C-4 or -5), 70.46 (C-3), 70.19 (C-2), 68.12 (C-4 or -5), 54.02 (OCH$_3$), 40.06 (C-6).

2R-aminomethyl-6S-methyl-3R,4R,5R-trihydroxy-tetrahydropyrane (12) was obtained as crude material from β-C-nitromethyl fucoside (Phiasivongsa P, Samoshin V, Gross P. *Tetrahedron Lett.* 2003, 44(29), 5495-5498.) (100 mg, 0.48 mmol).

N-(6S-Methyl-3R,4R,5R-trihydroxy-tetrahydropyranosyl-2R-methyl)-cinnamide (13) Crude 2R-aminomethyl-6S-methyl-3R,4R,5R-trihydroxy-tetrahydropyrane (12, 85 mg), triethylamine (100 uL, 0.72 mmol) and EDC*HCl (138 mg, 0.72 mmol) were dissolved in dry DMF (1.5 mL) and MeOH (1 mL) and cooled to 0° C. Then, cinnamic acid (85.3 mg, 0.576 mmol) dissolved in DMF (0.5 mL) was added dropwise under argon and the reaction was subsequently allowed to warm to room temperature and was stirred for 22 h. The reactions was quenched with saturated aqueous NH$_4$Cl (20 mL), and extracted with EtOAc (1×60 mL, 5×20 mL). The combined organic layers were dried over Na$_2$SO$_4$, filtered and concentrated in vacuo. The residue was purified by chromatography on silica (CH$_2$Cl$_2$/EtOH, gradient of 0-20%) and the title compound was obtained as amorphous solid (48.8 mg, 33% over two steps).

$^1$H NMR (400 MHz, MeOH-d4) δ 7.60-7.50 (m, 3H, 2×ArH, olefin-H), 7.42-7.32 (m, 3H, ArH), 6.69 (d, J=15.8 Hz, 1H, olefin-H), 3.70-3.59 (m, 4H, THP-H-5, -6, CH$_2$), 3.50-3.44 (m, 2H, THP-H-3, -4), 3.30-3.24 (m, 1H, THP-H-2), 1.26 (d, J=6.4 Hz, 3H, CH$_3$).

$^{13}$C NMR (101 MHz, MeOH-d4) δ 169.10 (C=O), 141.84 (olefin-CH), 136.32 (ArC), 130.81 (ArCH), 129.94 (2C, ArCH, 128.81 (2×C, ArCH), 121.73 (olefin-CH), 79.83 (THP-C-2), 76.19 (THP-C-3 or -4), 75.72 (THP-C-6), 73.62 (THP-C-5), 69.50 (THP-C-3 or -4), 41.95 (CH$_2$), 17.17 (CH$_3$). (Note: THP stands for tetrahydropyran)

HRMS: [C$_{16}$H$_{21}$NO$_5$+H]$^+$ calcd: 308.14925 found: 308.14885

Example 3

Evaluation of the Mannose- and Fucose-Based Library for LecB Binding

In the fluorescence polarization assay, mannose- and fucose-derived amides/sulfonamides showed binding to LecB (Tables 2 to 6), displacing the fucose-derived reporter ligand 3 in a competitive manner. The amides bound to LecB having up to 10-fold better affinity to the protein than methyl mannoside.

In Tables 2 to 5, rIC$_{50}$s are relative to MeMan as the standard in the fluorescence polarization assay on each plate. rIC$_{50}$s in bold face are calculated relative to Me-α-Man (IC$_{50}$ of MeMan and IC$_{50}$ of Fuc, see legend FIG. 1). Values below 1 means a stronger ligand than Me-α-Man (bold face).

Example 4

Determination of the Binding Thermodynamics of Mannose-Derived Inhibitors to LecB by Isothermal Calorimetry The cinnamide 11a, was analyzed by microcalorimetry (Table 1) and the stronger affinity to LecB than methyl mannoside was confirmed (K$_d$=21.6 μM). The enthalpy of binding is slightly reduced compared to methyl mannoside (difference of 0.3 kcal/mol), possibly resulting from a suboptimal hydrogen bond formation. The entropy of binding, however, is increased by 0.8 kcal/mol, compared to methyl mannoside. This may be accounted for a release of loosely bound water molecules at the protein surface, as well as a beneficial removal of an unstructured solvation of the ligand upon binding.

TABLE 1

Determination of the binding thermodynamics of mannose-derived inhibitors to LecB by isothermal calorimetry (data for 11a and Me-α-D-Man represent average of two measurements)

| Compound | $K_a$ [$M^{-1}$] | $K_d$ [μM] | ΔH [kcal/mol] | TΔS [kcal/mol] | N |
|---|---|---|---|---|---|
| 11a (cinnamide) | 46250 | 21.6 | −2.9 | 3.4 | 1.03 |
| Me-α-D-Man | 15150 | 66.0 | −3.2 | 2.6 | 1.09 |

Example 5

Inhibition of Agglutination

Figure 2:
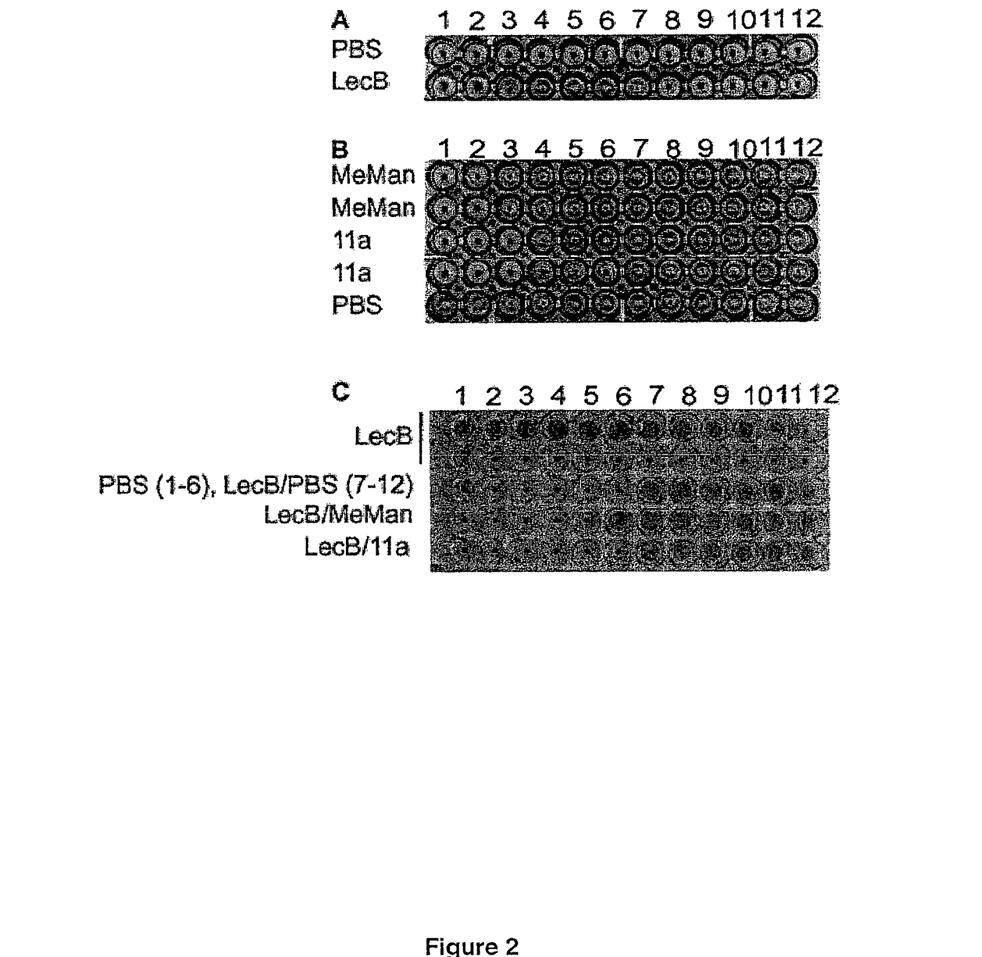
FIG. 2. A. Agglutination of *S.cerevisiae* by serial dilutions of LecB; B. Inhibition of agglutination of LecB (13 μg/mL) and *S. cerevisiae* with serial dilutions (1 mM to 133 nM) of methyl-a-D-mannoside and 11a; C. Hemagglutination of papain treated sheep eryhrocytes by serial dilutions of LecB (initial concentration 1.25 mg/mL LecB, serial dilution 1:2, lines 1 and 2), the buffer control (line 3 columns 1-6); Inhibition of agglutination of LecB and sheep erythrocytes with serial dilutions of methyl-a-D-mannoside (1.33 mM to 178 nM, line 4) and 11a (1.33 mM to 178 nM, line 5) and the buffer control (line 3, columns 7-12).

Lectins agglutinate cells via their different carbohydrate binding sites in the oligomeric assembly (LecB is a homotetramer). LecB is known to hemagglutinate erythrocytes from various organisms. Since LecB binds fucose-residues and mannosides, *Saccharomyces cerivisiae*, an organism (yeast) with highly mannosylated surface glycans, was used in a known model system for agglutination of mannose-binding lectins. In this assay, LecB was able to agglutinate the yeast cells (FIG. 2A). This agglutination could then be disrupted by addition of inhibitors of LecB. Methyl mannoside served as a control molecule, disrupting the agglutination at 444 μM, and 11a was tested and proved to be a better inhibitor (inhibition of agglutination at 197 μM) for agglutination than methyl mannoside, consistent with data from the aforementioned biochemical assay (i.e., fluorescence polarization assay) and microcalorimetry experiments (FIG. 2B). Hemagglutination of sheep erythrocytes gave a similar trend at generally lower concentrations than methyl mannoside (FIG. 2C): methyl mannoside and 11a inhibited agglutination of LecB and sheep erythrocytes at 113 μM and 23 μM, respectively.

Hemagglutination experiments were conducted with LecB as described by Kadam et al. for LecA (Kadam R U, Bergmann M, Hurley M, Garg D, Cacciarini M, Swiderska M A, Nativi C, Sattler M, Smyth A R, Williams P, Cámara M, Stocker A, Darbre T, Reymond J. A *Angew Chem Int Ed Engl.* 2011, 50(45), 10631-5.) Sheep red blood cells were obtained from Thermo Fisher Scientific (Germany). For the yeast agglutination, PBS-washed *S. cerevisiae* strain ss328 was used instead of sheep red blood cells, without papain treatment.

TABLE 2

Mannose-derived libraries of sulfonamides as LecB inhibitors

| $R_1$ | $R_3$ | compound | $IC_{50\,[\mu M]}$ | $rIC_{50}$ (MeMan) |
|---|---|---|---|---|
| H | H | 10a | 19 | 0.09 |
| H | Me | 10b | 68.2 | 0.31 |
| H | Br | 10c | 24.9 | 0.12 |
| H | $NO_2$ | 10d | 47.4 | 0.21 |
| Me | Me | 10e | 3.2 | 0.015 |
| iPr | iPr | 10f | 11.5 | 0.05 |

TABLE 3

Mannose-derived libraries of amides as LecB inhibitors

| $R_1$ | $R_2$ | $R_3$ | compound | $IC_{50\,[\mu M]}$ | $rIC_{50}$ (MeMan) |
|---|---|---|---|---|---|
| H | H | H | 11a | 66.95 | 0.3 |
| OMe | H | H | 11b | 45.8 | 0.21 |
| $NO_2$ | H | H | 11c | 75.455 | 0.35 |
| $NH_2$ | H | H | 11d | 52.6 | 0.24 |
| Me | H | H | 11e | 62.7 | 0.29 |
| H | $NO_2$ | H | 11f | 53.4 | 0.25 |
| H | $NH_2$ | H | 11g | 63 | 0.29 |
| H | H | OMe | 11h | 66.05 | 0.3 |
| H | H | $NO_2$ | 11i | 106.3 | 0.49 |
| H | H | $NH_2$ | 11j | 53.2 | 0.24 |
| H | H | Me | 11k | 36.1 | 0.16 |
| H | H | Cl | 11l | 48.4 | 0.22 |
| Cl | H | Cl | 11m | 71 | 0.32 |
| H | OMe | OMe | 11n | 28 | 0.13 |
| H | $R_2, R_3$ = methylenedioxy | | 11o | 31.8 | 0.15 |

TABLE 4

Mannose-derived libraries of amides as LecB inhibitors

| R | compound | $IC_{50\,[\mu M]}$ | $rIC_{50}$ (MeMan) |
|---|---|---|---|
| Ph | 11p | 203.15 | 0.93 |
| $CH_2Ph$ | 11q | 204.7 | 0.93 |
| p-$NO_2$—$C_6H_4$ | 11r | 206.3 | 0.94 |
| o-Cl—$C_6H_4$ | 11s | 238.6 | 1.09 |
| 2-naphtyl | 11t | 118.0 | 0.54 |

TABLE 5

Fucose-derived amide as LecB inhibitors

| compound | IC$_{50}$ [µM] | rIC$_{50}$ (MeMan) |
|---|---|---|
| 13 | 20.2 | 0.1 |

TABLE 6

Mannose- and fucose-derived sulfonamides as LecB inhibitors

| compound | IC$_{50}$ [µM] |
|---|---|
|  13b | 1 |
|  14 | 79 |
|  15 | 12.7 |

Example 6

Analysis of the Interaction of Compounds of the Present Invention with LecB by Surface Plasmon Resonance The measurements were run on a GE Biacore X100 as single cycle injections of 5 different concentrations. CM5 chips were activated with EDC/NHS and streptavidin was covalently coated to the surface. Subsequently, biotinylated LecB was captured and inhibitors were injected using aqueous buffer (10 mM HEPES, 150 mM NaCl, 0.05% Tween20 and pH 7.4). The fit of the experimental sensogram was performed using a 1:1 binding model (see Table 7).

TABLE 7

| compound | K$_d$ [µM] | k$_a$ [1/M*s] | k$_d$ [1/s] |
|---|---|---|---|
| 11n | 7.7 µM | 170 | 0.0013 |
| 13 | 1.61 µM | 255 | 0.00041 |
| 13b | 324 nM | 1263 | 0.00041 |

The invention claimed is:

1. A compound represented by the following general formula (I) or a salt thereof:

$$R^1\text{-}N(R^2)\text{-}X\text{-}R^3 \quad (I)$$

wherein X is SO$_2$ or CO;
R$^1$ is

(II) or (III) [fucose-derived sugar structures with linker -(CH$_2$)$_n$-]

n is 1, 2 or 3;
R$^2$ is a hydrogen atom or an alkyl group having 1 to 3 carbon atoms;
R$^3$ is
(i) an aralkenyl group or an aralkyl group, the alkenyl moiety being substituted or unsubstituted and having 2 to 6 carbon atoms, the alkyl moiety being substituted or unsubstituted and having 1 to 6 carbon atoms and the aryl moiety may have one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group, and wherein two adjacent substituents of the aryl moiety may be connected to form a methylenedioxy group or an ethylenedioxy group;
(ii) an aryl group or a heteroaryl group, both of which may have one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group, wherein two adjacent substituents of the aryl group may be connected to form a methylenedioxy group or an ethylenedioxy group, and wherein if R$^1$ is formula (III), R$^2$ is a hydrogen atom and X is CO, R$^3$ is not an o-nitrophenyl group; or
(iii) a heteroaralkenyl group or a heteroaralkyl group, the alkenyl moiety being substituted or unsubstituted and having 2 to 6 carbon atoms, the alkyl moiety being substituted or or unsubstituted and having 1 to 6 carbon atoms and the heteroaryl moiety may have one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group; and R$^4$ is a C$_1$-C$_4$ alkyl group or an aryl group, wherein when n is 2, the moiety of the formula (II) or (III) many be substituted with a hydroxyl group.

2. The compound according to claim 1, wherein n is 1 and/or R$^2$ is a hydrogen atom.

3. The compound according to claim 1, wherein R$^4$ is a methyl group, an ethyl group or a phenyl group.

4. The compound according to claim 1, wherein the aryl moiety, the heteroaryl moiety, the aryl group or the heteroaryl group of R$^3$ may have one or more substituents selected from the group consisting of a halogen atom, —NH$_2$, —NO$_2$ and a methoxy group, or two adjacent substituents of the aryl moiety or the aryl group may be connected to form a methylenedioxy group or an ethylenedioxy group.

5. The compound according to claim 1, wherein the aryl moiety or the aryl group is a phenyl group or a naphthyl group.

6. The compound according to claim 1, wherein X is SO$_2$.

7. The compound according to claim 1, wherein X is C=O.

8. The compound according to claim 1, wherein X is SO$_2$ and R$^3$ is represented by the formula (IV):

(IV)

wherein R$^6$ to R$^{10}$ are independently selected from the group consisting of a hydrogen atom, a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group; or wherein either R$^6$ and R$^7$, or R$^7$ and R$^8$, or R$^8$ and R$^9$, or R$^9$ and R$^{10}$ are connected to form a methylenedioxy group or ethylenedioxy group.

9. The compound according to claim 1, wherein X is C=O and R$^3$ is represented by the formula (V):

(V)

wherein R$^6$ to R$^{10}$ are independently selected from the group consisting of a hydrogen atom, a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group; or wherein either R$^6$ and R$^7$, or R$^7$ and R$^8$, or R$^8$ and R$^9$, or R$^9$ and R$^{10}$ are connected to form a methylenedioxy group or an ethylenedioxy group.

10. The compound according to claim 1, wherein R$^1$ is represented by formula (II) or formula (III), and n is 1.

11. The compound according to claim 1, represented by the following formulae (VI) to (XV):

(VI)

(VII)

(VIII)

(IX)

(X)

(XI)

(XII)

(XIII)

(XIV)

(XV)

12. A pharmaceutical composition comprising the compound according to claim 1, and optionally comprising one or more constituents selected from the group consisting of a pharmaceutically acceptable carrier, a diluent, an excipient and an anti-bacterial therapeutic agent.

13. A method for treatment of a *Pseudomonas aeruginosa* infection in a patient, said method comprising administering a compound according to claim 1 to a patient in need of treatment of *Pseudomonas aeruginosa* infection, optionally in combination with one or more anti-bacterial therapeutic agents.

14. The method according to claim 13, wherein said *Pseudomonas aeruginosa* infection is an *Pseudomonas aeruginosa*-associated respiratory tract infection and wherein said in a patient is suffering from cystic fibrosis.

15. A compound represented by the following formula (XVI):

(XVI)

wherein n is 1, 2 or 3 and $R^{11}$ is a $C_1$-$C_4$ alkoxy group or —$NH_2$.

* * * * *